(12) United States Patent
Lee et al.

(10) Patent No.: US 12,144,593 B2
(45) Date of Patent: Nov. 19, 2024

(54) APPARATUS AND METHOD FOR MEASURING MULTIPLE BIO-SIGNALS USING IMAGE SENSOR BASED ON DIFFERENT BINNING SIZES

(71) Applicant: SAMSUNG ELECTRONICS CO., LTD., Suwon-si (KR)

(72) Inventors: Jong Wook Lee, Suwon-si (KR); Byung Hoon Ko, Hwaseong-si (KR); Yong Joo Kwon, Yongin-si (KR); Seung Woo Noh, Seongnam-si (KR); Hyun Seok Moon, Hwaseong-si (KR); Sung Mo Ahn, Yongin-si (KR); Kun Sun Eom, Yongin-si (KR); Tak Hyung Lee, Seoul (KR); Myoung Hoon Jung, Bucheon-si (KR); Chang Mok Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 657 days.

(21) Appl. No.: 17/354,091

(22) Filed: Jun. 22, 2021

(65) Prior Publication Data
US 2022/0265149 A1     Aug. 25, 2022

(30) Foreign Application Priority Data
Feb. 25, 2021   (KR) .................. 10-2021-0025879

(51) Int. Cl.
*A61B 5/0205*     (2006.01)
*A61B 5/00*        (2006.01)
(Continued)

(52) U.S. Cl.
CPC ........ *A61B 5/0205* (2013.01); *A61B 5/02007* (2013.01); *A61B 5/02108* (2013.01);
(Continued)

(58) Field of Classification Search
CPC .. A61B 5/02416; A61B 5/1455; A61B 5/0059
See application file for complete search history.

(56) References Cited

U.S. PATENT DOCUMENTS

| 8,254,523 B2 | 8/2012 | Takekoshi |
| 8,508,637 B2 | 8/2013 | Han et al. |

(Continued)

FOREIGN PATENT DOCUMENTS

| EP | 3 057 486 A1 | 8/2016 | |
| EP | 3057486 B1 * | 5/2017 | ........... A61B 5/0059 |

(Continued)

OTHER PUBLICATIONS

Communication dated Nov. 29, 2022 issued by the Korean Intellectual Office in Korean Application No. 10-2021-0025879.
(Continued)

*Primary Examiner* — Joel Lamprecht
*Assistant Examiner* — Nyrobi Celestine
(74) *Attorney, Agent, or Firm* — Sughrue Mion, PLLC

(57) ABSTRACT

An apparatus for measuring bio-signals is provided. According to an example embodiment, the apparatus for measuring bio-signals includes: a light source configured to emit light onto an object; an image sensor including: a pixel array configured to detect the light emitted by the light source and reacted by the object and a pixel binning unit configured to bin data of the light, detected by the pixel array, by using at least two different binning sizes; and a processor configured to acquire a plurality of bio-signals respectively based on data of the at least two different binning sizes, which are output from the image sensor.

11 Claims, 12 Drawing Sheets

(a)                                    (b)

(51) Int. Cl.
*A61B 5/02* (2006.01)
*A61B 5/021* (2006.01)
*A61B 5/024* (2006.01)
*A61B 5/1172* (2016.01)
*A61B 5/145* (2006.01)
*A61B 5/1455* (2006.01)
*A61B 5/16* (2006.01)
*H04N 25/46* (2023.01)

(52) U.S. Cl.
CPC ........ *A61B 5/02416* (2013.01); *A61B 5/1172* (2013.01); *A61B 5/14532* (2013.01); *A61B 5/14546* (2013.01); *A61B 5/1455* (2013.01); *A61B 5/165* (2013.01); *A61B 5/4866* (2013.01); *A61B 5/4875* (2013.01); *A61B 5/6803* (2013.01); *A61B 5/681* (2013.01); *A61B 5/6898* (2013.01); *H04N 25/46* (2023.01)

(56) References Cited

U.S. PATENT DOCUMENTS

| | | | |
|---|---|---|---|
| 8,537,971 | B2 | 9/2013 | Takekoshi |
| 9,741,158 | B2 | 8/2017 | Kim et al. |
| 10,045,702 | B2 | 8/2018 | Jeanne et al. |
| 10,203,816 | B2 | 2/2019 | Nelson et al. |
| 10,203,826 | B2 | 2/2019 | Nelson et al. |
| 10,203,827 | B2 | 2/2019 | Nelson et al. |
| 10,203,828 | B2 | 2/2019 | Nelson et al. |
| 10,257,447 | B2 | 4/2019 | Zhou |
| 11,234,647 | B2 | 2/2022 | Kang et al. |
| 2005/0218332 | A1* | 10/2005 | Rutten ............... H04N 5/32 348/E3.02 |
| 2006/0187324 | A1* | 8/2006 | Lin ............... H04N 23/6812 348/241 |
| 2010/0157103 | A1 | 6/2010 | LeGall et al. |
| 2011/0013040 | A1 | 1/2011 | Han et al. |
| 2013/0327950 | A1* | 12/2013 | Niwa ............... G01T 1/17 250/336.1 |
| 2014/0240492 | A1* | 8/2014 | Lee ............... H04N 25/135 348/136 |
| 2014/0263964 | A1 | 9/2014 | Yang et al. |
| 2016/0066863 | A1 | 3/2016 | Thaveeprungsriporn et al. |
| 2016/0235312 | A1 | 8/2016 | Jeanne et al. |
| 2017/0302866 | A1* | 10/2017 | Fu ............... H04N 25/772 |
| 2019/0290146 | A1 | 9/2019 | Schipper et al. |
| 2020/0054289 | A1 | 2/2020 | Shimol et al. |
| 2020/0359900 | A1 | 11/2020 | Yan et al. |
| 2022/0008009 | A1 | 1/2022 | Kang et al. |

FOREIGN PATENT DOCUMENTS

| | | |
|---|---|---|
| EP | 3 603 507 A1 | 2/2020 |
| JP | 2006145362 A | 6/2006 |
| JP | 201130778 A | 2/2011 |
| JP | 2015201164 A | 11/2015 |
| JP | 2018502492 A | 1/2018 |
| JP | 2020130772 A | 8/2020 |
| KR | 1020140137935 A | 12/2014 |
| KR | 1020180000159 A | 1/2018 |
| KR | 1020180044198 A | 5/2018 |
| KR | 1020200014523 A | 2/2020 |
| KR | 1020200029906 A | 3/2020 |
| KR | 1020200133112 A | 11/2020 |
| WO | 2014/024104 A1 | 2/2014 |
| WO | 2020/162805 A1 | 8/2020 |

OTHER PUBLICATIONS

Communication issued Jan. 26, 2022 by the European Patent Office in European Patent Application No. 21189352.4.

* cited by examiner (a)　　　　　　(b)　　　　　　(c)

APPARATUS AND METHOD FOR MEASURING MULTIPLE BIO-SIGNALS USING IMAGE SENSOR BASED ON DIFFERENT BINNING SIZES

CROSS-REFERENCE TO RELATED APPLICATION(S)

This application claims priority from Korean Patent Application No. 10-2021-0025879, filed on Feb. 25, 2021, in the Korean Intellectual Property Office, the entire disclosure of which is incorporated by reference herein for all purposes.

BACKGROUND

1. Field

Example embodiments of the present disclosure relate to technology for measuring multiple bio-signals using an image sensor.

2. Description of Related Art

A complementary metal oxide semiconductor (CMOS) image sensor (CIS) is a device that converts an optical signal into an electrical signal, and is mainly used in cameras for capturing photos or moving images. Recently, for measuring bio-signals such as photoplethysmography (PPG), the CMOS image sensor may be used to replace a photo-diode (PD) which is a light receiver. When bio-signals are measured using the CIS, a change of bio-signals according to positions in the field of view (FOV) of the CIS may be measured.

Such spatial resolution depends on resolution according to the physical number of pixels of the image sensor, and depends on the use of binning that combines adjacent pixels together for reading signals. When the CIS is used for measuring bio-signals, binning is mainly used to increase a signal-to-noise ratio (SNR). Further, in the case where temporal resolution, expressed in the sampling rate, is important instead of high spatial resolution, binning may be used to reduce the amount of data. Thus, the temporal resolution and the spatial resolution are in a trade-off relationship. Accordingly, in order to measure health indicators which require high temporal resolution and high spatial resolution, there is a need for a method of controlling the temporal resolution and the spatial resolution efficiently.

SUMMARY

According to an aspect of an example embodiment, there is provided an apparatus for measuring multiple bio-signals, the apparatus including: a light source configured to emit light onto an object; an image sensor including: a pixel array configured to detect the light emitted by the light source and reacted by the object and a pixel binning unit configured to bin data of the light, detected by the pixel array, by using at least two different binning sizes; and a processor configured to acquire a plurality of bio-signals respectively based on data of the at least two different binning sizes, which are output from the image sensor.

The image sensor may include a complementary metal-oxide semiconductor (CMOS) image sensor.

The apparatus may further include a binning pattern generator configured to generate an optimal binning pattern, the optimal binning pattern including a binning size and a time to apply the binning size, with respect to each of the plurality of bio-signals.

The binning pattern generator may be configured to transmit the optimal binning pattern to the pixel binning unit.

The binning pattern generator may be further configured to generate the optimal binning pattern based on at least one of a resolution, a frame rate, or a signal-to-noise ratio (SNR), that is required for each of the plurality of bio-signals.

The pixel binning unit may be further configured to, based on the optimal binning pattern, alternatively perform binning of the at least two different binning sizes on the data of the detected light at least twice or more.

The pixel binning unit may be further configured to, based on the optimal binning pattern, perform, on the data of the detected light, binning of a first binning size in a first interval, and perform binning of a second binning size in a second interval following the first interval.

The processor may be further configured to acquire a bio-signal using data of a first binning size, and the processor may be further configured to obtain missing data of the first binning size in an interval, in which binning is performed with a second binning size, by performing interpolation based on data of the first binning size that is adjacent to the interval.

The processor may be further configured to acquire a bio-signal using data of a first binning size, and the processor may be further configured to obtain missing data of the first binning size in an interval, in which binning is performed with a second binning size, by combining data of the second binning size in the interval.

The plurality of bio-signals may include bio-signals to be used for obtaining bio-information, the bio-information including at least two of heart rate, blood pressure, triglyceride, fingerprint, vascular age, arterial stiffness, aortic pressure waveform, stress index, fatigue level, carotenoid, blood glucose, cholesterol, calories, protein, intracellular % ater, extracellular water, and uric acid.

According to an aspect of an example embodiment, there is provided an apparatus for measuring bio-signals, the apparatus including: a light source configured to emit light onto an object; an image sensor including: a pixel array configured to detect the light emitted by the light source and reacted by the object; and a pixel binning unit configured to bin data of the light, detected by the pixel array, by using at least two different binning sizes; a binning controller configured to control in real time changing of a binning size of the pixel binning unit; and a processor configured to acquire a plurality of bio-signals by using data of the at least two different binning sizes, which are output from the image sensor.

The apparatus may further include a binning pattern generator configured to determine a pattern of a binning size to be applied in each interval with respect to each of the plurality of bio-signals, and the binning controller may be further configured to, based on the data output by the image sensor and the binning size to be applied in each interval, generate a control signal for controlling in real time the changing of the binning size, and transmit the control signal to the pixel binning unit.

The binning controller may be further configured to estimate a current interval of the data output from the image sensor, and generate a control signal based on a pattern of a binning size corresponding to the estimated current interval.

With respect to a periodically repeated waveform of which data is obtained from the detected light, the binning controller may be further configured to generate a control signal such that binning is performed with an equal binning size in a same interval of each period.

With respect to a periodically repeated waveform of which data is obtained from the detected light, the binning controller may be further configured to generate a control signal such that binning is performed alternately with the at least two different binning sizes in a same interval of each period.

The processor may be further configured to obtain a fingerprint image by using data of a first binning size, and based on the obtained fingerprint image, the processor is further configured to determine a contact position of the object or perform user authentication, and based on the contact position of the object being normal or the user authentication being successful, the binning controller may be further configured to generate a control signal for changing the binning size to a second binning size to acquire a bio-signal other than the fingerprint image.

The processor may be further configured to acquire a bio-signal using data of a first binning size, and the processor may be further configured to obtain missing data of the first binning size in an interval, in which binning is performed with a second binning size, by performing interpolation based on data of the first binning size that is adjacent to the interval.

The processor may be further configured to acquire a bio-signal using data of a first binning size, and the processor may be further configured to obtain missing data of the first binning size in an interval, in which binning is performed with a second binning size, by combining data of the second binning size in the interval.

According to an aspect of an example embodiment, there is provided a method of measuring bio-signals, the method including: emitting, by using a light source, light onto an object; detecting light emitted by the light source and reacted by the object; binning data of the detected light by using at least two different binning sizes and outputting the binned data; and acquiring a plurality of bio-signals by using the output data of the at least two different binning sizes.

The acquiring the plurality of bio-signals may include: obtaining missing data of a first binning size in an interval, in which binning is performed with a second binning size, by performing interpolation based on data of the first binning size that is adjacent to the interval; and acquiring a bio-signal using data of the first binning size, including obtained missing data.

The acquiring the plurality of bio-signals may include: obtaining missing data of a first binning size in an interval, in which binning is performed with a second binning size, by combining data of the second binning size in the interval; and acquiring a bio-signal based on data of the first binning size, including the obtained missing data.

According to an aspect of an example embodiment, there is provided an electronic device including: a main body in which an apparatus for measuring a bio-signal is provided; and an output interface configured to output a processing result of the apparatus for measuring the bio-signal, wherein the apparatus for measuring the bio-signal includes: an image sensor including a pixel array configured to detect light emitted by a light source and reacted by an object, and a pixel binning unit configured to bin data of the light, detected by the pixel array, by using at least two different binning sizes and output the binned data; a binning controller configured to control in real time changing of a binning size by the pixel binning unit; and a processor configured to acquire a first bio-signal by using data of a first binning size output from the pixel binning unit, and to acquire a second bio-signal by using data of a second binning size.

The electronic device may include at least one of a wristwatch-type wearable device, an ear-wearable device, a necklace-type wearable device, or a smartphone.

The first bio-signal may include a fingerprint image, and based on the fingerprint image, the processor may be further configured to determine a contact position of the object or perform user authentication.

Based on the contact position of the object being normal or the user authentication being successful, the binning controller may be further configured to generate a control signal for changing the binning size to the second binning size, and transmit the control signal to the pixel binning unit The binning controller may be further configured to control the pixel binning unit to perform binning with the first binning size at least twice or more, and the processor is further configured to determine the contact position of the object based on the binning with the first binning size at least twice or more.

The output interface may be further configured to, based on the contact position of the object not being normal, output guide information for guiding a user to change the contact position.

The second bio-signal may include a photoplethysmography (PPG) signal for obtaining a blood pressure, and the processor may be further configured to acquire the PPG signal by using data of the second binning size, and obtain the blood pressure based on the acquired PPG signal.

The processor may be further configured to acquire the PPG signal by using data of the second binning size, and the processor may be further configured to obtain missing data of the second binning size in an interval, in which binning is performed with the first binning size, by performing interpolation based on data of the first binning size that is adjacent to the interval.

The electronic device may further include a force sensor disposed above or below the image sensor, wherein the processor is further configured to obtain the blood pressure based on the PPG signal and a contact force obtained by the force sensor.

BRIEF DESCRIPTION OF THE DRAWINGS

The above and other aspects, features, and advantages of example embodiments of the disclosure will be more apparent from the following detailed description taken in conjunction with the accompanying drawings, in which.

DETAILED DESCRIPTION

Figure 1:
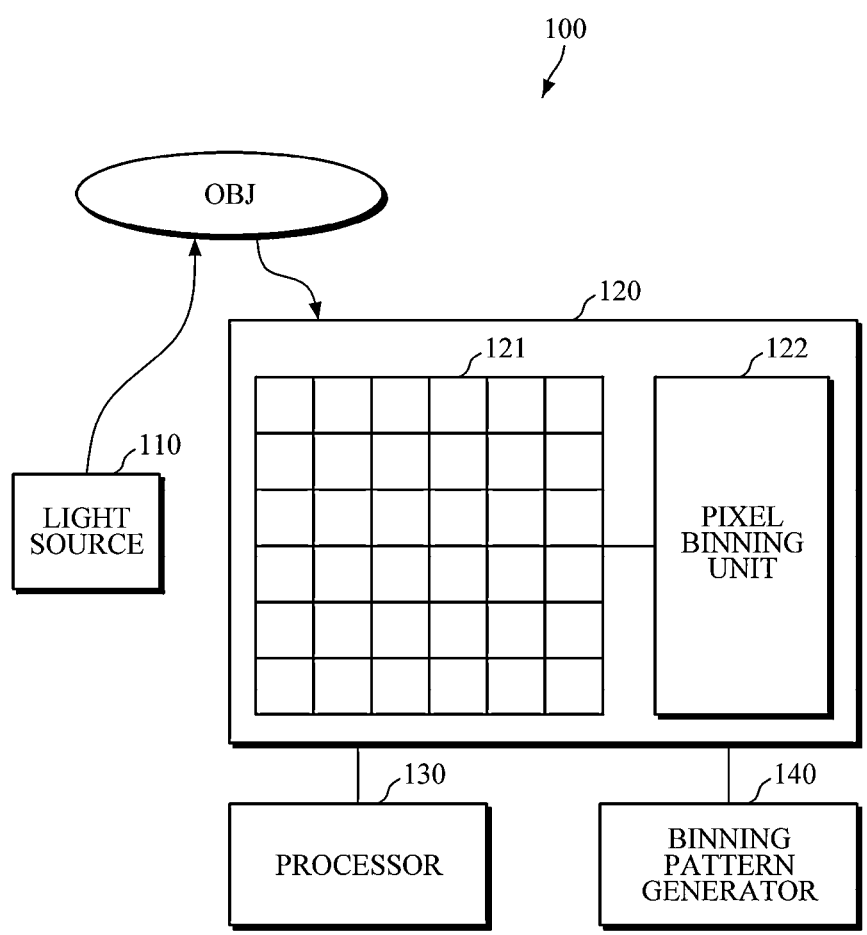
FIG. 1 is a block diagram illustrating an apparatus for measuring multiple bio-signals according to an example embodiment.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Figure 2:
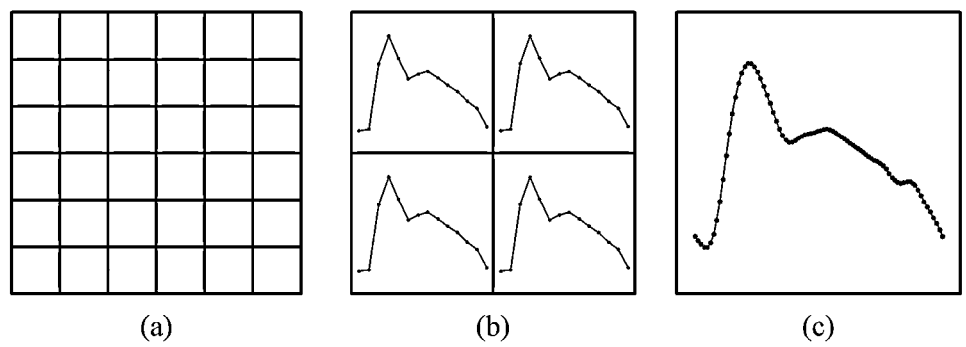
FIG. 2 is a diagram explaining a binning operation of an image sensor of FIG. 1.
Figure 3:
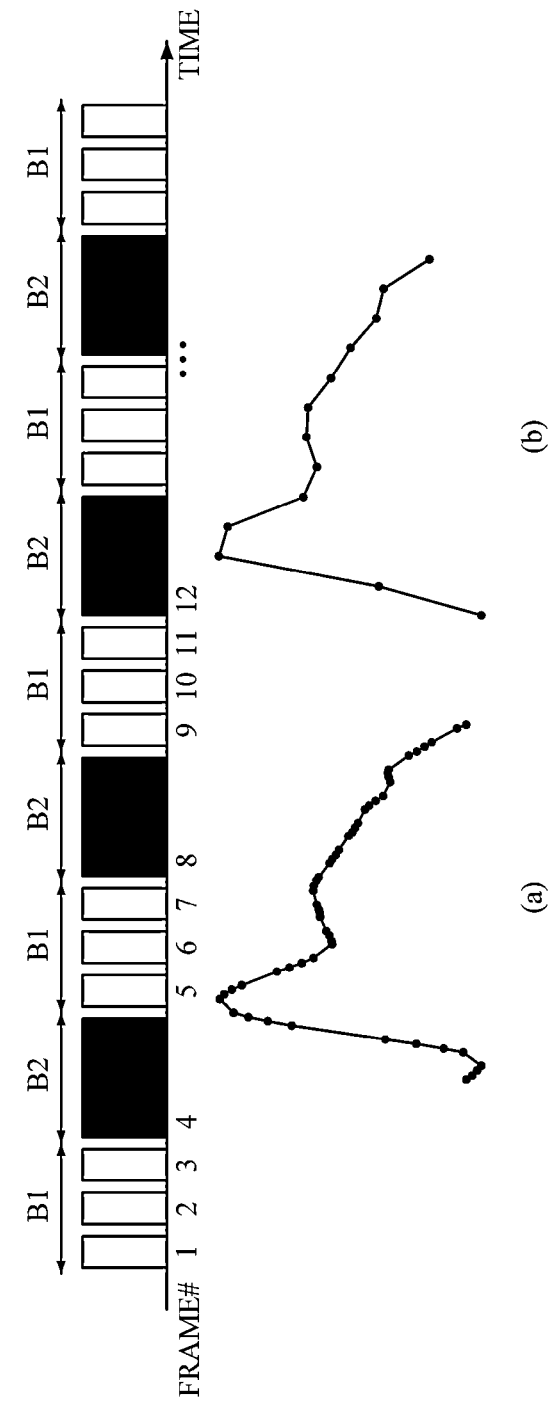
FIG. 3 is a diagram explaining operations of a pixel binning unit and a processor of FIG. 1.

FIG. 1 is a block diagram illustrating an apparatus for measuring multiple bio-signals according to an example embodiment. FIG. 2 is a diagram explaining a binning operation of an image sensor of FIG. 1. FIG. 3 is a diagram explaining operations of a pixel binning unit and a processor of FIG. 1.

Referring to FIG. 1, an apparatus 100 for measuring multiple bio-signals includes a light source 110, an image sensor 120, a processor 130, and a binning pattern generator 140.

The light source 110 may emit light onto an object OBJ. In this case, the object may be a body part at which a bio-signal may be easily measured, and may be, for example, an inner part of the wrist that is adjacent to the radial artery or an upper part of the wrist where veins or capillaries are located, or a peripheral part of the body, such as fingers, toes, etc., where blood vessels are densely distributed. The light source 110 may be a light emitting diode (LED), a laser diode (LD), a phosphor, or a combination thereof. The light source 110 may emit light of two or more wavelengths penetrating into different depths of the object OBJ. For example, the light source 110 may emit light of a short wavelength which penetrates to a shallow depth into the object, e.g., a green wavelength range of 500 nm to 565 nm capable of penetrating into capillaries, and may emit light of a long wavelength which penetrates to a relatively long depth into the object OBJ, e.g., an infrared wavelength range of 750 nm to 2500 nm capable of penetrating into arterioles. However, the light source 110 is not limited thereto and may emit light of various other wavelengths such as a blue wavelength, a red wavelength, and the like.

The image sensor 120 is an electronic device for generating an electrical signal by detecting light, which reacts with the object OBJ by being scattered or reflected from or transmitted into the object OBJ after the light is emitted by the light source 110. The image sensor 120 may include a pixel array 121 and a pixel binning unit 122. In this case, the image sensor 120 may be a Complementary Metal Oxide Semiconductor (CMOS) image sensor.

The pixel array 121 may accumulate an electric charge by detecting light, reacting with the object OBJ, according to a driving signal. Further, the pixel array 121 may generate pixel data by detecting a potential change due to the accumulated electric charge, and may transmit the generated pixel data to the pixel binning unit 122. As illustrated herein, the pixel array 121 may include a plurality of pixels arranged in pixel rows and pixel columns, e.g., a plurality of pixels arranged in a 6×6 matrix. In this case, the number of pixel rows or the number of pixel columns may vary according to a size of a form factor and the like. Each pixel may include a photoelectric conversion device (not shown), and a plurality of transistors (not shown) for processing photo charges output from the photoelectric conversion device. In this case, the photoelectric conversion device may be implemented as a photo diode, a photo transistor, a photogate, a pinned photo diode, and the like.

The pixel binning unit 122 may bin pixel data, output from the pixel array 121, to a preset binning size and may output the binned pixel data. While the pixel array 121 detects data for measuring multiple bio-signals, the pixel binning unit 122 may bin the pixels to two or more different binning sizes according to an optimal binning pattern generated by the binning pattern generator 140. In this case, the optimal binning pattern may be set based on requirements of each bio-signal, and may include information, e.g., a binning size for each bio-signal, a sequence and time to apply the binning size, and/or a number of times to repeat the binning size, and the like. In this case, requirements of each bio-signal may include, e.g., resolution, frame rate, signal-to-noise ratio (SNR), and the like.

The image sensor 120 may interact with an external device, e.g., the processor 130 and/or the binning pattern generator 140, a display device (not shown), etc., through a provided interface (not shown). Further, the image sensor 120 may further include a data output interface (not shown) before or after the pixel binning unit 122, in which the data output interface outputs data by converting binning data in analog form output from the pixel array 121 or binning data in analog form output from the pixel binning unit 122, into digital data, and/or by amplifying the data. The data output interface (not shown) may include an analog-digital converter (ADC) and/or an amplifier.

The processor 130 may acquire two or more bio-signals by using data of two or more binning sizes, which are output from the image sensor 120. In this case, the bio-signals may refer to signals to be used for obtaining bio-information, such as heart rate, blood pressure, triglyceride, fingerprint, vascular age, arterial stiffness, aortic pressure waveform, stress index, fatigue level, carotenoid, blood glucose, cholesterol, calories, protein, intracellular water, extracellular water, uric acid, and the like. However, the bio-information is not limited thereto. For convenience of explanation, the following terms may be used: a heart rate signal may be used to refer to a signal for obtaining a heart rate; a blood pressure signal or a photoplethysmography (PPG) signal may be used to refer to a signal for obtaining blood pressure; and a fingerprint image may be used to refer to a signal for obtaining a fingerprint. Upon acquiring each bio-signal, the processor 130 may obtain bio-information by using the acquired each bio-signal.

For example, the processor 130 may acquire a first bio-signal (e.g., heart rate signal) by using frame data binned to a first binning size, and may acquire a second bio-signal (e.g., blood pressure signal) by using frame data binned to a second binning size. In this case, while the first bio-signal is acquired using data of the first binning size, i.e., data of the first binning size for an interval, data of the first binning size is missing at an interval in which binning is performed with a second binning size for acquiring the second bio-signal (hereinafter referred to as a "missing interval"). The processor 130 may obtain data of the first binning size at the missing interval by complementing the data using various pre-defined methods; and vice versa for the data of the second binning size at its missing interval. For example, the processor 130 may obtain the data of the first binning size for the missing interval by interpolation using data of the first binning size of frames adjacent to the missing interval. In another example, the processor 130 may obtain any one of data (e.g., a minimum value, a maximum value, a median value, a value of any frame, etc.) of the second binning size in the missing interval, or a value (e.g., average) combined using a pre-defined linear and/or non-linear combination equation(s), as data of the first binning size for the missing interval.

The binning pattern generator 140 may generate an optimal binning pattern to be applied while data is detected by the image sensor 120, and may transmit the optimal binning pattern to the image sensor 120 in advance before data is detected by the pixel array 121 of the image sensor 120. In this case, the optimal binning pattern may include information, such as a binning size for each bio-signal, a sequence and time to apply the binning size, and/or a number of times to repeat the binning size, and the like, and may be set using requirements of each bio-signal, e.g., resolution, frame rate, signal-to-noise ratio (SNR), and the like.

Referring to FIG. 2, assuming that the pixel array 121 includes pixels arranged in a 6×6 matrix as illustrated herein, (a) shows an example of obtaining data at a low sampling rate for each pixel without performing binning; (b) shows an example of obtaining data at a relatively higher sampling rate than (a) by performing 3×3 binning; and (c) shows an example of obtaining data at a very high sampling rate, although spatial decomposition is impossible, by performing 6×6 binning.

For example, during measurement of a heart rate and blood pressure, a large binning size, e.g., a binning size of 6×6 as illustrated in (c), may be set so that data with relatively low spatial resolution (i.e., high sampling rate) may be detected for measuring the heart rate; and a relatively small binning size, e.g., a binning size of 3×3 as illustrated in (b), may be set so that data with relatively high spatial resolution (i.e., low sampling rate) may be detected for measuring the blood pressure. In this embodiment, as described above, the processor 130 may acquire two or more bio-signals having various requirements, by properly controlling temporal resolution and spatial resolution which are in a trade-off relationship.

The binning pattern generator 140 may determine a sequence and time to apply a binning size determined for each bio-signal, and/or a number of times to repeat the binning size, and the like. In this case, the binning pattern generator 140 may determine a sequence and time to apply a binning size determined for each bio-signal, and/or a number of times to repeat the binning size, and the like by considering a shape of a waveform of data obtained from the object, a measurement time, each user's characteristics, and the like.

For example, the binning pattern generator 140 may determine the sequence and time to apply a binning size, and/or a number of times to repeat the binning size, and the like, so that binning of each binning size may be performed alternately at least twice or more. In another example, binning of the first binning size may be performed in a first interval, and binning of the second binning size may be performed in a second interval following the first interval. In yet another example, binning of the first binning size and binning of the second binning size may be performed alternately in one of the first and second intervals, and only one of the binning operations of the first binning size and the second binning size may be performed in the other one of the first and second intervals. However, the binning operation is not limited thereto.

FIG. 3 is a diagram illustrating an optimal binning pattern which is set so that an interval B1 of a first binning size (e.g., 6×6 binning) and an interval B2 of a second binning size (e.g., 3×3 binning) may be alternately repeated at a frame ratio of 3:1. For example, the processor 130 may acquire a first bio-signal ((a) of FIG. 3) by using frame data 1, 2, 3, 5, 6, 7, 9, 10, 11, . . . of the first binning size which are output from the image sensor 120, and may acquire a second bio-signal ((b) of FIG. 3) by using frame data 4, 8, 12, . . . of the second binning size.

In this case, for a missing interval while the first bio-signal is acquired, i.e., an interval B2 in which binning is performed with the second binning size, the processor 140 may perform interpolation by using data of the first binning size of frames adjacent to the missing interval. For example, for the fourth frame, in which binning is performed with the second binning size in FIG. 3, the processor 130 may perform interpolation by using data of frames (e.g., third and fifth frames) adjacent to the first binning interval. In this case, the number of adjacent preceding or succeeding frames is not limited to one. Alternatively, by averaging data of the second binning size in the missing interval, in which binning is performed with the second binning size, the processor 130 may obtain the averaged data as data of the first binning size for the missing interval. For example, for the fourth frame in which binning is performed with the second binning size, data of four pixel regions are output by 3×3 binning, such that by averaging the output data of the four pixel regions, the processor 130 may obtain the averaged value as the data of the first binning size (6×6) for the fourth frame. However, this is merely an example.

Figure 4:
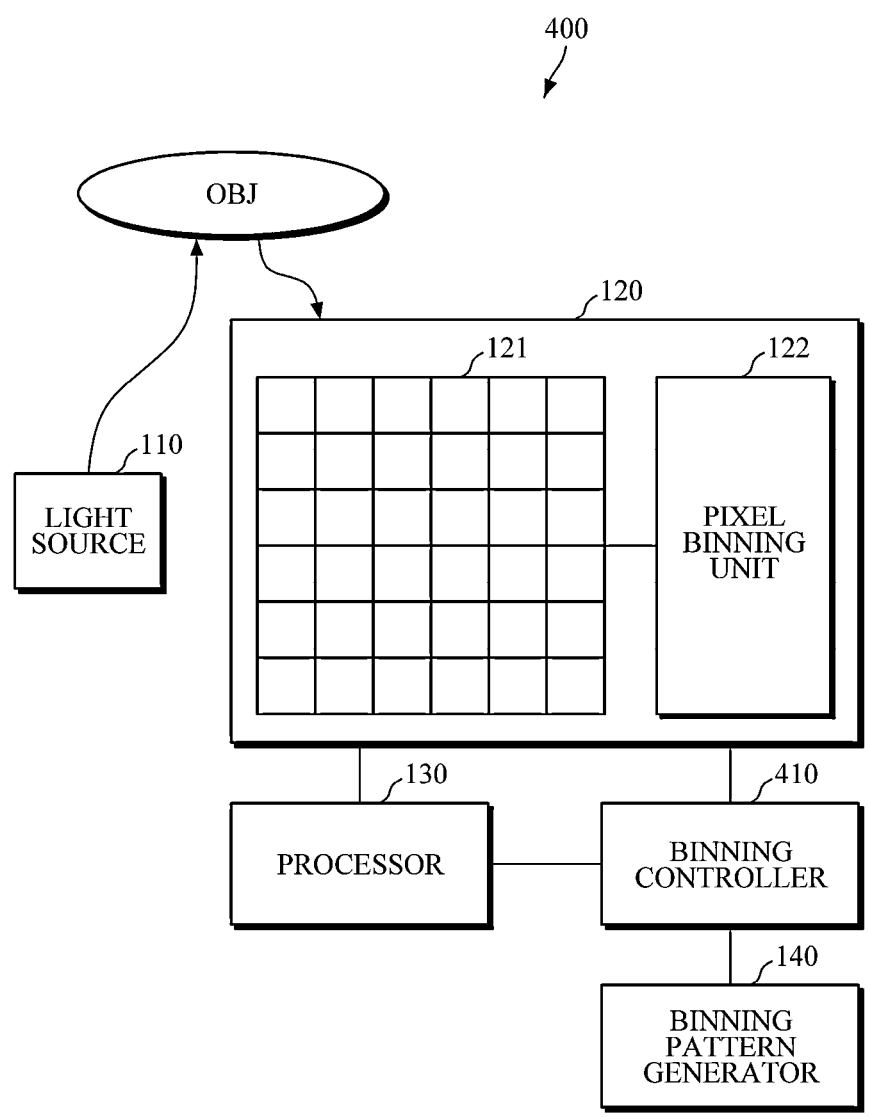
FIG. 4 is a block diagram illustrating an apparatus for measuring multiple bio-signals according to an example embodiment.
Figure 5:
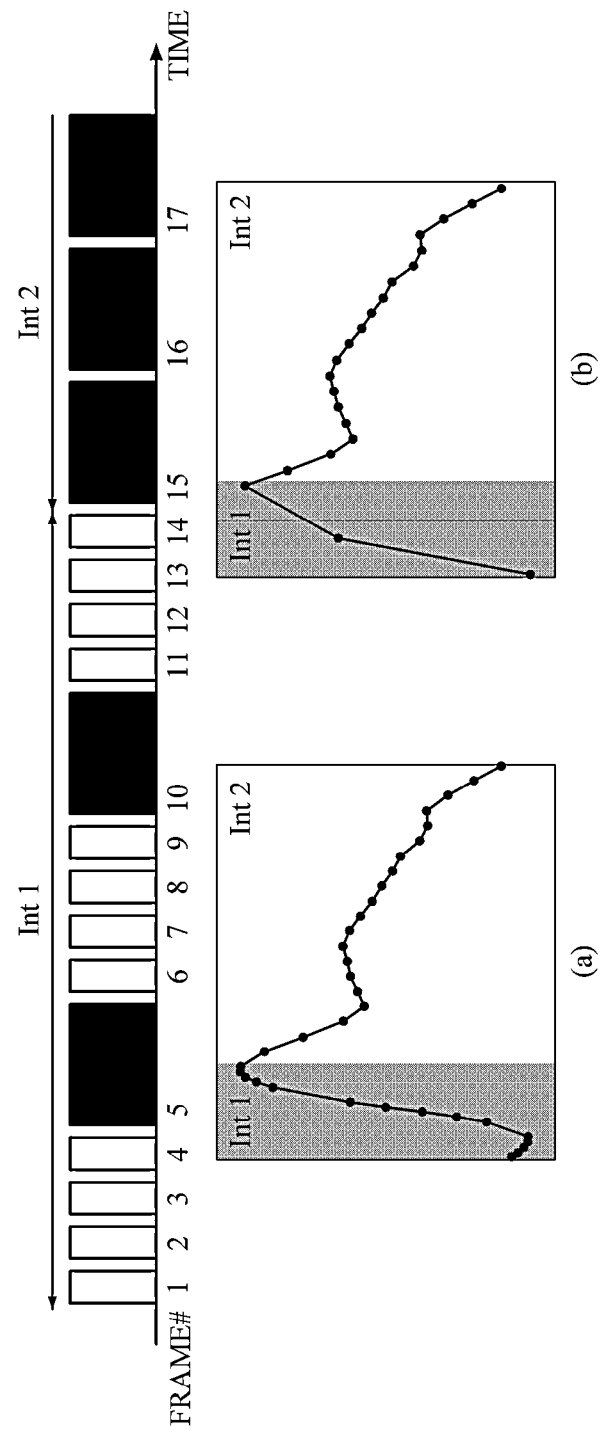
FIG. 5 is a diagram explaining operations of a pixel binning unit and a processor of FIG. 4.

FIG. 4 is a block diagram illustrating an apparatus for measuring multiple bio-signals according to an example embodiment. FIG. 5 is a diagram explaining operations of a pixel binning unit and a processor of FIG. 4.

Referring to FIG. 4, the apparatus 400 for measuring multiple bio-signals includes the light source 110, the image sensor 120, the processor 130, the binning pattern generator 140, and a binning controller 410. The light source 110, the image sensor 120, the processor 130, and the binning pattern generator 140 are described above in detail, and thus will be briefly described below.

As described above, the light source 110 may be formed as one or more LEDs, LDs, phosphors, or a combination thereof, and may emit light onto the object under the control of the processor 130.

The image sensor 120 may detect light reacting with the object, and may convert the light into an electrical signal and output the signal. As described above, the image sensor 120 may include a plurality of pixel arrays 121 for detecting light reacting with the object, and the pixel binning unit 122 for binning data of light, detected at each pixel, with two or more different binning sizes and outputting the data. The pixel binning unit 122 may change in real time a binning size under the control of the binning controller 410 while the pixel array 121 detects the data.

In response to an input of multiple bio-signals to be measured, which are preset in the apparatus or are input from a user, an external device, etc., the binning pattern generator 140 may determine a binning size for each bio-signal and an interval to apply the binning size based on requirements of each bio-signal. The binning pattern generator 140 may divide, for each bio-signal, an interval which is important in a data waveform and an interval which is relatively not important, and may set a sequence and time to apply the binning size and/or a number of times to repeat the binning size, and the like, so that binning of a binning size determined for the bio-signal may be mainly performed in the interval important for the bio-signal.

Referring to FIG. 5, in order to measure, for example, a heart rate signal, data of the first interval Int 1, in which a waveform rises, is more important such that a sampling rate may be increased by mainly using 6×6 binning in the first interval Int 1, but in order to also measure a blood pressure signal, 6×6 binning and 3×3 binning may be set alternately. In the second interval Int2, in which a waveform falls, 3×3 binning may be set for measuring the blood pressure signal.

The above example is merely illustrative, and a pattern to apply a binning size may be set variously by considering various conditions such as a number of bio-signals to be obtained, a measurement time, and the like. For example, binning may be performed by using only a binning size that is important for a bio-signal in each interval; or while performing binning by using all of preset binning sizes in all of the intervals, binning may be performed by using a binning size that is relatively important for a bio-signal in each interval may be mainly performed. Alternatively, in the case of a periodically repeated waveform, such as a PPG, binning may be performed with an equal binning size in the same interval of each period. In this case, if high temporal resolution and high spatial resolution are required at the same time in the same interval, binning may be performed alternately with different binning sizes in the same interval of each period.

The binning controller 410 may control in real time changing of a binning size of the pixel binning unit 122 by using information, such as a binning size for each bio-signal, an interval and/or pattern to apply the binning size, and the like which are generated by the binning pattern generator 140. The binning controller 410 may generate a control signal and may transmit the generated control signal to an interface (e.g., general-purpose input/output (GPIO) pin, etc.) provided in the image sensor 120. Once frame data are output from the image sensor 120, the binning controller 410 may estimate a current interval, and may control the pixel binning unit 122 by generating a control signal based on a pattern of a binning size corresponding to the current interval.

For example, referring to FIG. 5, the binning controller 140 may transmit a control signal for a binning size of 6×6 to the pixel binning unit 122 before data detection, and may estimate a current interval by using output frame data. If the current interval is the first interval Int 1, the binning controller 140 may transmit a control signal for changing a fifth frame to a binning size of 3×3. As described above, if the current interval is the first interval Int 1, the binning controller 140 transmits a control signal for changing a binning size to the pixel binning unit 122 so that 6×6 binning and 3×3 binning may be performed alternately. Upon determining that the current interval is a second interval Int 2, the binning controller 140 may transmit a control signal for changing a binning size to the pixel binning unit 122 so that 3×3 binning may be performed continuously.

The processor 130 may obtain two or more bio-signals by using data of two or more binning sizes output from the image sensor 120, and may obtain data of missing intervals (e.g., fifth and tenth frames in FIG. 5), in which binning is performed with different binning sizes to acquire different bio-signals, by interpolation and the like. Referring to FIG. 5, (a) illustrates a heart rate signal, in which missing data for the heart rate signal in the first interval Int 1 may be obtained by interpolation using adjacent frame data for a heart rate signal, or by averaging blood pressure signal data of the missing intervals (fifth and tenth frames). Further, in the second interval Int 2, only 3×3 binning is performed for the blood pressure signal, such that by averaging data output for the respective frames, the processor 130 may obtain the averaged data as the heart rate signal data. In FIG. 5, (b) illustrates a blood pressure signal, in which data of the missing intervals (1-4, 6-9, and 11-14 frames) may be obtained by interpolation using data of adjacent frames or by averaging data of the corresponding frames.

In one embodiment, multiple bio-signals may include other types of bio-signals, such as a blood pressure signal, a fingerprint image for user authentication or for tracking a contact position of an object, and the like. In order to perform user authentication before acquiring other bio-signals or to determine whether a contact position of the object is normal, the binning pattern generator 140 may set a predetermined interval at an initial stage of measurement to a first binning size for obtaining a fingerprint image, and may set a subsequent interval to a second binning size. In another example, in order to track whether the contact position of the object is changed midway during measurement, the binning pattern generator 140 may set an interval such that an operation may be performed with the first binning size at least twice or more during the entire measurement process, or may set an interval (e.g., diastolic interval) after a predetermined time in which an operation may be performed with the first binning size.

The processor 130 may obtain a fingerprint image by using data of the first binning size, and may perform user authentication or determine the contact position of the object by using the fingerprint image. If user authentication fails, the processor 130 may provide guide information on the failure of user authentication by using an output device (e.g., display, sound device, haptic device, etc.). If the contact position of the object is not in a normal range, the processor 130 may output information on the contact position of the object by using the output device. Further, the processor 130 may track a change in contact position of the object based on the fingerprint image, and if the contact position is changed midway, the processor 130 may correct a blood pressure value according to a degree of change of the contact position, or may output, through the output device, information indicating that accuracy of the blood pressure value is reduced due to a changed contact position.

If the processor 130 performs user authentication or determines that the contact position of the object is normal, the binning controller 410 may generate a control signal for changing a binning size in real time by referring to a binning size pattern set by the binning pattern generator 140, and may transmit the generated control signal to the pixel binning unit 122.

Figure 6:
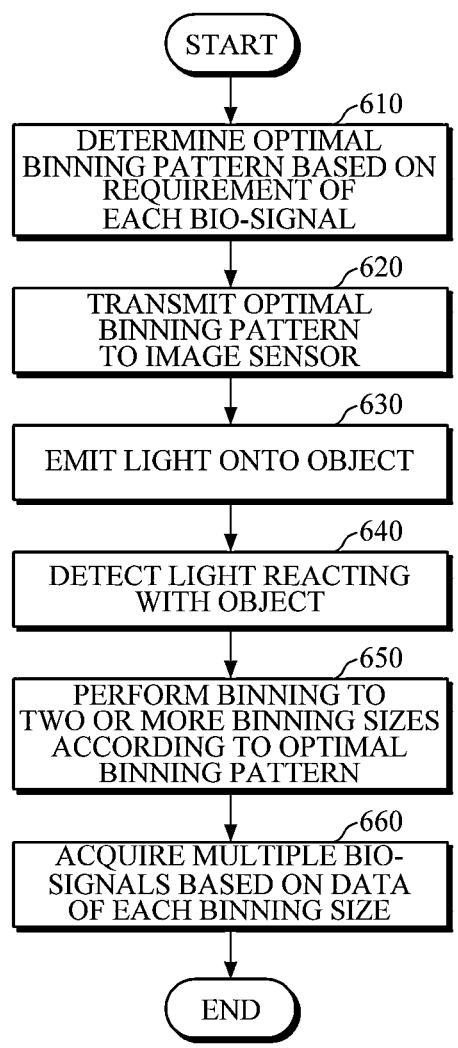
FIG. 6 is a flowchart illustrating a method of measuring multiple bio-signals according to an example embodiment.

FIG. 6 is a flowchart illustrating a method of measuring multiple bio-signals according to an example embodiment.

FIG. 6 is an example of a method of measuring multiple bio-signals which is performed by the apparatus 100 for measuring multiple bio-signals, which is described in detail above and thus will be briefly described below.

First, the apparatus 100 for measuring multiple bio-signals may determine an optimal binning pattern, including a binning size for each bio-signal, a time to apply the binning size, and the like, based on requirements of the respective multiple bio-signals in 610. In this case, the requirements of the respective bio-signals may include resolution, frame rate, signal-to-noise ratio (SNR), and the like.

Then, the apparatus 100 for measuring multiple bio-signals may transmit the determined optimal binning pattern to the image sensor in 620.

Subsequently, the apparatus 100 for measuring multiple bio-signals may emit light onto an object by using a light source in 630. The light source may be formed with one or more LEDs, LDs, phosphors, etc., and may emit light of multiple wavelengths.

Next, the apparatus 100 for measuring multiple bio-signals may detect light, reacting with the object, by using the image sensor in 640; and according to the optimal binning pattern, the apparatus 100 for measuring multiple bio-signals may perform binning on data of a frame, detected in 640, to a corresponding binning size in 650.

Then, the apparatus 100 for measuring multiple bio-signals may acquire multiple bio-signals by using data output from the image sensor with two or more binning sizes in 660. For example, by using data of the first binning size and data of the second binning size, the apparatus 100 for measuring multiple bio-signals may acquire the first bio-signal and the second bio-signals respectively corresponding to data of the first binning size and data of the second binning size, and data in the missing interval when the respective bio-signals are acquired may be obtained by interpolation using adjacent data or by averaging data output with different binning sizes in the missing interval, as described above.

Figure 7:
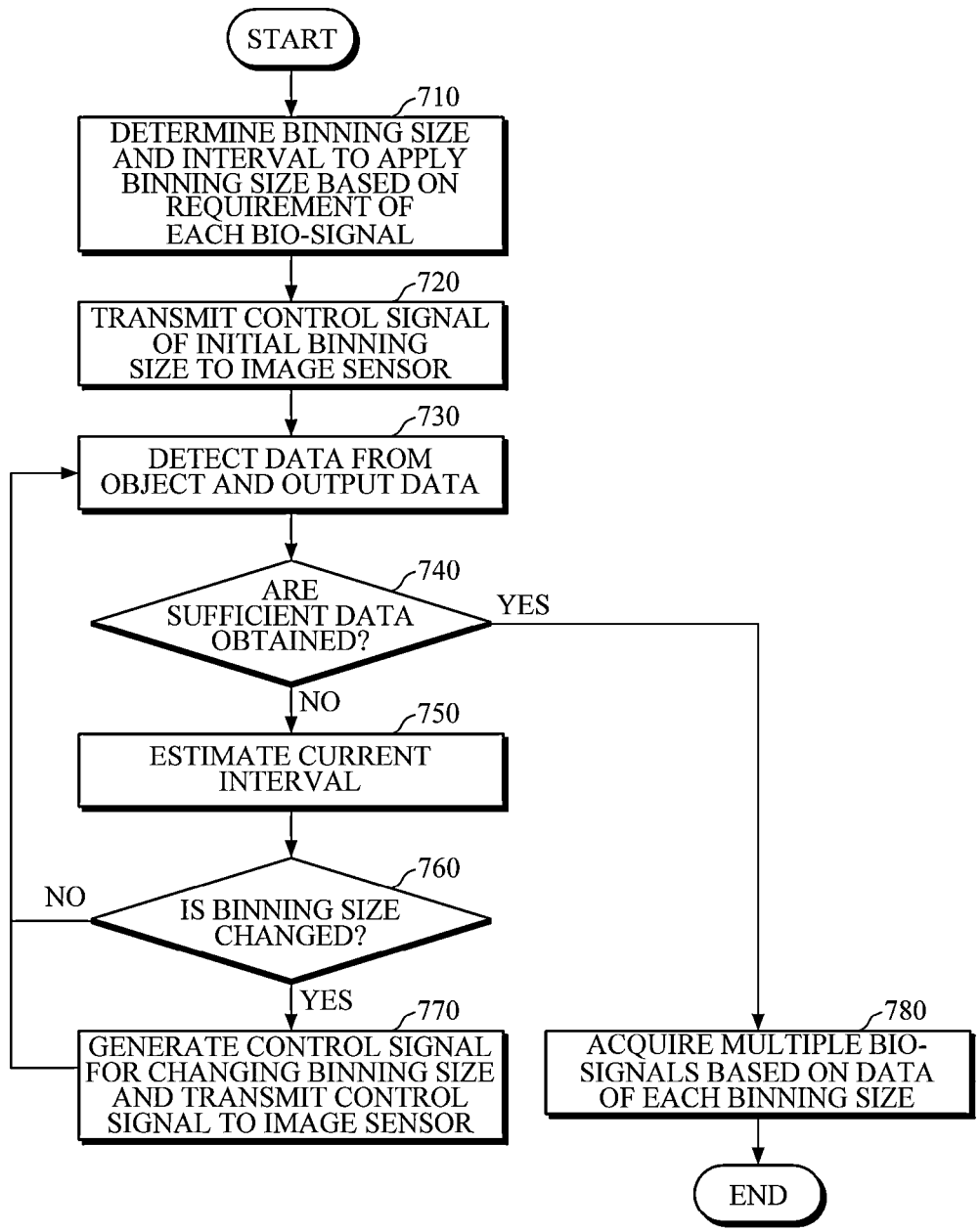
FIG. 7 is a flowchart illustrating a method of measuring multiple bio-signals according to an example embodiment.

FIG. 7 is a flowchart illustrating a method of measuring multiple bio-signals according to an example embodiment.

FIG. 7 is an example of a method of measuring multiple bio-signals which is performed by the apparatus 400 for measuring multiple bio-signals, which is described in detail above and thus will be briefly described below.

First, based on the respective requirements of the multiple bio-signals to be measured, the apparatus 100 for measuring bio-signals may determine a binning size for each bio-signal, an interval to apply the binning size, and the like in 710.

Then, the apparatus 100 for measuring bio-signals may transmit a control signal of an initial binning size to be applied at an initial detection stage to the image sensor in 720.

Subsequently, the apparatus 100 for measuring bio-signals may emit light onto an object by using a light source, may detect data from the object by using the image sensor, and may bin data of each detected frame with the applied binning size and output the binned data in 730.

Next, the apparatus 100 for measuring multiple bio-signals may determine whether data detected so far are sufficient to acquire multiple bio-signals in 740. For example, if data are detected up to a predetermined threshold or more, the apparatus 100 for measuring multiple bio-signals may determine that data are sufficient to acquire multiple bio-signals.

Then, upon determining in 740 that sufficient data are not yet obtained, the apparatus 100 for measuring multiple bio-signals may estimate a current interval based on the output data in 750.

Subsequently, the apparatus 100 for measuring multiple bio-signals may determine, in 760, whether it is required to change a binning size in the current interval estimated by using information such as a binning size, an interval to apply the binning size, and the like which are determined in 710. If it is required to change the binning size, the apparatus 100 for measuring multiple bio-signals may generate a control signal for changing a binning size and may transmit the control signal to the image sensor in 770 and may proceed to operation 730; and if it is not required to change the binning size, the apparatus 100 for measuring multiple bio-signals may proceed to operation 730 of continuously detecting data and performing a binning operation with a current binning size.

Next, upon determining in 740 that sufficient data are obtained, the apparatus 100 for measuring multiple bio-signals may acquire multiple bio-signals by using data of each binning size in 780. In this case, when acquiring the respective bio-signals, data of a missing interval may be obtained by interpolation using adjacent data, or by averaging data output with different binning sizes in the missing interval, and the like.

Figure 8:
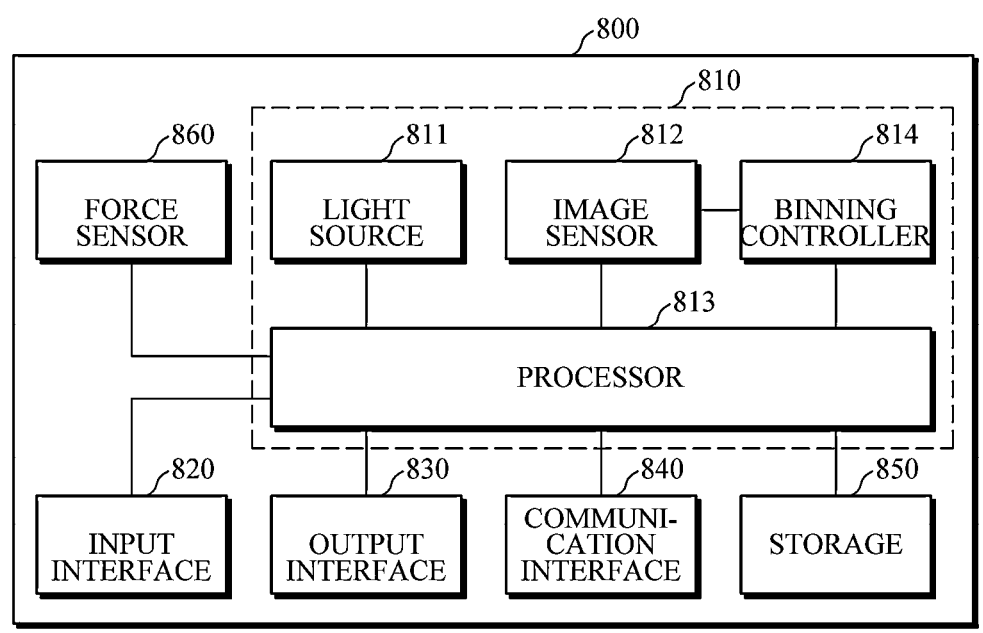
FIG. 8 is a block diagram illustrating an example of an electronic device including an apparatus for measuring multiple bio-signals according to an example embodiment.
Figure 9:
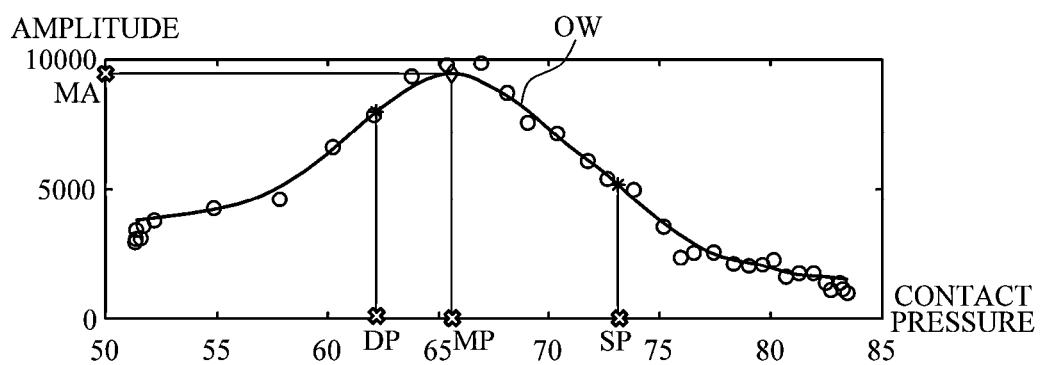
FIG. 9 is a diagram illustrating an example of an oscillometric waveform envelope for estimating blood pressure.

FIG. 8 is a block diagram illustrating an example of an electronic device including an apparatus for measuring multiple bio-signals according to an example embodiment. FIG. 9 is a diagram illustrating an example of an oscillometric waveform envelope for estimating blood pressure.

The electronic device 800 may include, for example, a wearable device of various types, such as a smart watch, a smart band, smart glasses, smart earphones, a smart ring, a smart patch, and a smart necklace, and a mobile device such as a smartphone, a tablet PC, and the like. Referring to FIG. 8, the electronic device 800 may include an apparatus 810 for measuring a bio-signal, an input interface 820, an output interface 830, a communication interface 840, a storage 850, and a force sensor 860 in a main body of the devices described above as examples. In addition, the electronic device 800 may further include an interface, an antenna module, a power management module, a camera module, a battery, and the like which are not illustrated herein.

The apparatus 810 for measuring a bio-signal, as an example of the aforementioned apparatuses 100 and 400 for measuring multiple bio-signals, may include a light source 811, an image sensor 812, a processor 813, and a binning controller 814. The binning controller 814 may be omitted if the apparatus 810 for measuring a bio-signal operates as the apparatus 100 for measuring multiple bio-signals of FIG. 1. A binning pattern generator (not shown) may be included as a component of the processor 813, and may be omitted if a type of bio-signal to be measured by the electronic device 800 is prestored, and information such as a binning size and the like is generated for each bio-signal by other device at the time of manufacture or at the initial time of use of the electronic device.

All the components of the apparatus 810 for measuring a bio-signal may be integrally mounted in the main body of a specific device described as an example. Alternatively, some components of the apparatus 810 for measuring a bio-signal may be distributed in two or more devices. For example, the light source 811 and the image sensor 812, used for detecting data from an object, may be mounted in a smart watch or a smart earphone, and the binning controller 814 for controlling in real time a binning operation of the image sensor 812 and the processor 813 for acquiring a bio-signal by using the detected data may be mounted in a smartphone to transmit and receive data with the smart watch or the smart earphone by wired or wireless communication. The respective components of the apparatus 810 for measuring a bio-signal may be used not only for the function of measuring a bio-signal but also for other functions performed by the electronic device 810.

The image sensor 812 may include a pixel array for detecting light reacting with the object after the light is emitted by the light source 811, and a pixel binning unit for binning the frame data, detected by the pixel array, with a corresponding binning size and outputting the data under the control of the binning controller 814 in real time.

The processor 813 may obtain two or more bio-signals by using data of two or more binning sizes output from the pixel binning unit, and may obtain bio-information by using the two or more bio-signals. In this case, when obtaining the respective bio-signals, data of the missing interval may be obtained by interpolation and the like, as described above.

Upon obtaining the multiple bio-signals, the processor 813 may obtain each bio-information independently by using the respective bio-signals. For example, the processor 813 may obtain the heart rate by using a heart rate signal and may obtain blood pressure by using a PPG signal. Alternatively, the processor 813 may obtain another bio-signal based on any one bio-signal. For example, the processor 813 may estimate blood pressure by using the heart rate obtained using the heart rate signal and features extracted from the PPG signal.

Once a fingerprint image is obtained, the processor 813 may extract fingerprint information (e.g., a fingerprint pattern, a fingerprint center point, etc.), and may track a contact position of an object and/or perform user authentication by using the fingerprint information. If the user authentication is successful or if the contact position is normal, the processor 813 may detect a blood pressure signal and/or estimate blood pressure. If the user authentication fails, the processor 813 may provide a user with guide information on the failure of authentication. In addition, if the contact position is not in a normal range or deviates from the normal range, the processor 813 may guide a user to adjust the contact position and the like or may correct a blood pressure value, or may provide guide information indicating that a blood pressure value is not correct.

Once the force sensor 860 measures a contact force between the image sensor 812 and the object, the processor 813 may estimate blood pressure based on oscillometry by using the contact force and the PPG signal.

FIG. 9 is a diagram illustrating an example of an oscillometric waveform envelope representing a relationship between contact pressure and amplitude of a PPG signal.

By using a pre-defined conversion equation, the processor 813 may convert the contact force into contact pressure, or if an area sensor is mounted in the electronic device 800, the processor 813 may obtain contact pressure by using the contact force and a contact area of the object measured by the area sensor.

The processor 813 may extract, e.g., a peak-to-peak point of the pulse wave signal waveform by subtracting a negative (−) amplitude value in3 from a positive (+) amplitude value in2 of a waveform envelope in1 at each measurement time of a PPG signal or a differential signal of the PPG signal, and may obtain an oscillometric waveform envelope (OW) by plotting the peak-to-peak amplitude at each measurement time against the contact pressure value at a corresponding time and by performing, for example, polynomial curve fitting.

The processor 813 may estimate mean arterial pressure (MAP), diastolic blood pressure (DBP), and systolic blood pressure (SBP) based on a contact pressure value MP at a maximum point MA of the pulse wave in the oscillometric waveform envelope OW, and contact pressure values DP and SP respectively at left and right points corresponding to amplitude values having a preset ratio (e.g., 0.5 to 0.7) to an amplitude value at the maximum point MA. The processor 813 may obtain the contact pressure values MP, DP, and SP as MAP, DBP, and SBP, respectively; or by using a pre-defined blood pressure estimation model, the processor 813 may estimate MAP, DBP, and SBP from the contact pressure values MP, DP, and SP, respectively. In this case, the blood pressure estimation equation may be expressed in the form of various linear and/or non-linear combination functions, such as addition, subtraction, division, multiplication, logarithmic value, regression equation, and the like, with no particular limitation.

The input interface 820 may receive a command and/or data to be used by each component of the electronic device 800, from a user and the like. The input interface 820 may include, for example, a microphone, a mouse, a keyboard, and/or a digital pen (e.g., a stylus pen, etc.).

The output interface 830 may output data generated or processed by the electronic device 800 by using visual and/or non-visual methods. The output interface 830 may include a sound output device, a display device, an audio module and/or a haptic module, and the like.

The sound output device may output sound signals to the outside of the electronic device 800. The sound output device may include, for example, a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device 800. The display device 800 may include, for example, a display, a hologram device, or a projector and control circuitry to control a corresponding one of the display, hologram device, and projector. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via an input device, or may output the sound via the sound output device, and/or a speaker and/or a headphone of an external electronic device directly or wirelessly connected to the electronic device 800.

A haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The communication interface 840 may support establishment of a direct (e.g., wired) communication channel and/or a wireless communication channel between the electronic device 800 and other electronic device within a network environment, and performing of communication via the established communication channel. The communication interface 840 may communicate with other electronic devices using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, and 3G, 4G, and 5G communications. However, these are merely examples and are not intended to be limiting.

The storage 850 may store various data to be used in components of the electronic device 800 for the operation of the electronic device 800. The various data may include, for example, software and input data and/or output data for a command related thereto, and the like. The storage 850 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 10:
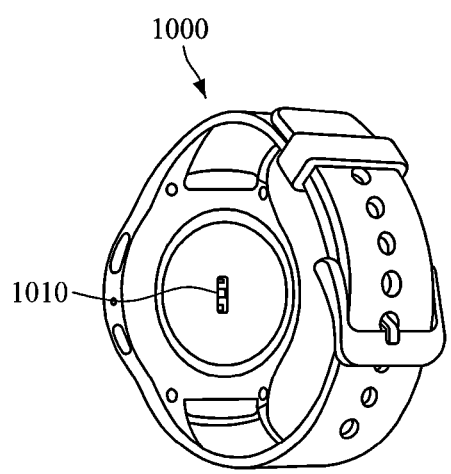
FIG. 10 is a diagram illustrating a wristwatch-type wearable device as an example of an electronic device according to an example embodiment.
Figure 11:
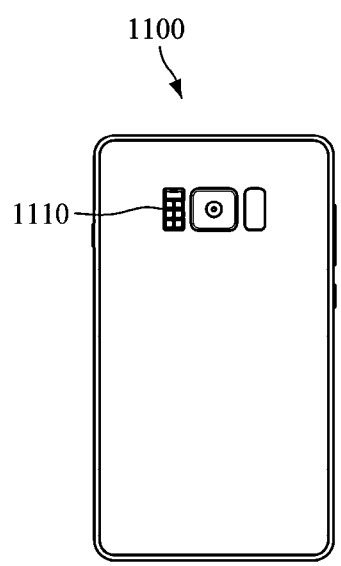
FIG. 11 is a diagram illustrating a mobile device as another example of an electronic device according to an example embodiment.
Figure 12:
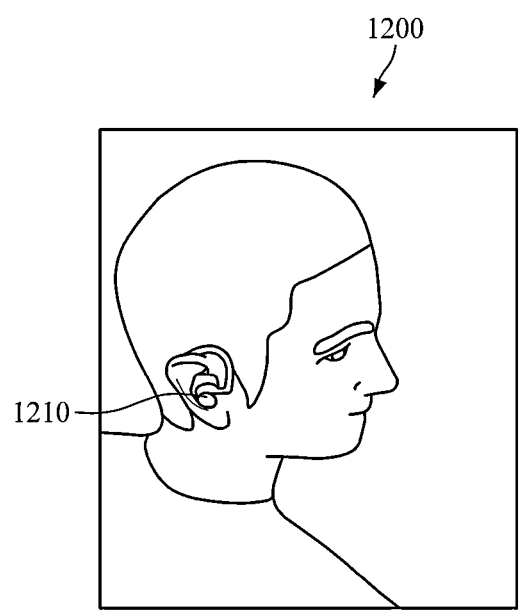
FIG. 12 is a diagram illustrating an ear-wearable device as yet another example of an electronic device according to an example embodiment.

FIGS. 10 to 12 are diagrams illustrating examples of structures of the electronic device of FIG. 8.

Referring to FIG. 10, the electronic device 800 may be implemented as a wristwatch-type wearable device 1000, and may include a main body and a wrist strap. A display is provided on a front surface of the main body, and may display various application screens, including time information, received message information, and the like. The light source 811 of the apparatus 810 for measuring a bio-signal and a sensor device 1010 such as the image sensor 812 may be disposed on a rear surface of the main body, and the processor 813 and/or the binning controller 814, electrically connected to the sensor device 1010 and configured to process a control signal and detected data, may be disposed in the main body.

Referring to FIG. 11, the electronic device 800 may be implemented as a mobile device 1100 such as a smartphone.

The mobile device 1100 may include a housing and a display panel. The housing may form an exterior of the mobile device 1100. The housing has a first surface, on which a display panel and a cover glass may be disposed sequentially, and the display panel may be exposed to the outside through the cover glass. The light source 811, and a sensor device 1110 such as the image sensor 812, a camera module, and/or an infrared sensor, etc. may be disposed on a second surface of the housing. When a user transmits a request for bio-information by executing an application stored in the mobile device 1100, the processor 813 and the binning controller 814, which are disposed in the main body and electrically connected to the sensor device 1010, acquire multiple bio-signals and estimate bio-information by using the sensor device 1110, and may provide the estimated bio-information as images and/or sounds to a user.

Referring to FIG. 12, the electronic device 800 may also be implemented as an ear wearable device 1200.

The ear-wearable device 1200 may include a main body and an ear strap. A user may wear the ear-wearable device 1200 by hanging the ear strap on a user's auricle. The ear strap may be omitted depending on a shape of the ear-wearable device 1200. The main body may be inserted into the external auditory meatus. The light source 813, and a sensor device 1210 such as the image sensor 812 may be mounted in the main body. The ear-wearable device 1200 may provide a bio-information estimation result as sounds to a user, or may transmit the estimation result to an external device, e.g., mobile device, tablet personal computer (PC), etc., through a communication module mounted in the main body.

The disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments needed for realizing the disclosure may be readily deduced by programmers of ordinary skill in the art to which the disclosure pertains.

At least one of the components, elements, modules or units (collectively "components" in this paragraph) represented by a block in the drawings may be embodied as various numbers of hardware, software and/or firmware structures that execute respective functions described above, according to an example embodiment. According to example embodiments, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

Although example embodiments have been described, it will be apparent to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. An apparatus for measuring bio-signals, the apparatus comprising:
   a light source configured to emit light onto an object;
   an image sensor comprising a pixel array configured to detect the light emitted by the light source and reacted by the object, the image sensor being configured to bin data of the light, detected by the pixel array, by using at least two different binning sizes; and a processor configured to acquire a plurality of bio-signals respectively based on data of the at least two different binning sizes, the data of the at least two different binning sizes being output from the image sensor, wherein the processor is further configured to acquire a first bio-signal using data of a first binning size in a first interval and acquire a second bio-signal using data of a second binning size in a second interval following the first interval, the first interval and the second interval being alternately repeated at a preset frame ratio, and wherein the processor is further configured to independently obtain first bio-information using the first bio-signal, which is acquired based on the first binning size in the first interval, and obtain second bio-information using the second bio-signal, which is acquired based on the second binning size in the second interval, the first bio-information being a different type of bio-information than the second bio-information.

2. The apparatus of claim 1, wherein the image sensor comprises a complementary metal-oxide semiconductor (CMOS) image sensor.

3. The apparatus of claim 1, wherein the image sensor is further configured to receive an optimal binning pattern, the optimal binning pattern including a binning size and a time to apply the binning size, with respect to each of the plurality of bio-signals.

4. The apparatus of claim 3, wherein the optimal binning pattern is determined based on at least one of a resolution, a frame rate, or a signal-to-noise ratio (SNR), that is required for each of the plurality of bio-signals.

5. The apparatus of claim 3, wherein the image sensor is further configured to, based on the optimal binning pattern, alternatively perform binning of the at least two different binning sizes on the data of the detected light at least twice or more.

6. The apparatus of claim 3, wherein the image sensor is further configured to, based on the optimal binning pattern, perform, on the data of the detected light, binning of the first binning size in the first interval, and perform binning of the second binning size in the second interval following the first interval.

7. The apparatus of claim 1, wherein the processor is further configured to obtain missing data of the first binning size in the second interval, in which binning is performed with the second binning size, by performing interpolation based on data of the first binning size that is adjacent to the second interval.

8. The apparatus of claim 1, wherein
the processor is further configured to obtain missing data of the first binning size in the second interval, in which binning is performed with the second binning size, by combining data of the second binning size in the second interval.

9. A method of measuring bio-signals, the method comprising:

emitting, by using a light source, light onto an object;

detecting light emitted by the light source and reacted by the object;

binning data of the detected light by using at least two different binning sizes and outputting the binned data; and acquiring a plurality of bio-signals by using the output data of the at least two different binning sizes, wherein the acquiring the plurality of bio-signals comprises acquiring a first bio-signal using data of a first binning size in a first interval and acquiring a second bio-signal using data of a second binning size in a second interval following the first interval, the first interval and the second interval being alternately repeated at a preset frame ratio, and wherein the method further comprises independently obtaining first bio-information using the first bio-signal, which is acquired based on the first binning size in the first interval, and obtaining second bio-information using the second bio-signal, which is acquired based on the second binning size in the second interval, the first bio-information being a different type of bio-information than the second bio-information.

10. The method of claim 9, wherein the acquiring the first bio-signal comprises:

obtaining missing data of the first binning size in the second interval, in which binning is performed with the second binning size, by performing interpolation based on data of the first binning size that is adjacent to the second interval; and acquiring the first bio-signal using data of the first binning size, including obtained missing data.

11. The method of claim 9, wherein the acquiring the first bio-signal comprises:

obtaining missing data of the first binning size in the second interval, in which binning is performed with the second binning size, by combining data of the second binning size in the second interval; and acquiring the first bio-signal based on data of the first binning size, including the obtained missing data.

* * * * *